United States Patent [19]

Davis

[11] Patent Number: 5,207,643
[45] Date of Patent: May 4, 1993

[54] MULTI-LUMEN-CATHETER FLOW VALVE SYSTEM

[75] Inventor: Richard C. Davis, Palm Harbor, Fla.

[73] Assignee: Ballard Medical Products, Draper, Utah

[21] Appl. No.: 696,928

[22] Filed: May 8, 1991

[51] Int. Cl.⁵ .......................... A61M 5/14; A61M 5/00
[52] U.S. Cl. ..................... 604/80; 604/248; 137/625.19; 137/625.46
[58] Field of Search ...................... 604/30, 32, 43, 246, 604/248, 258, 283, 280, 284, 33, 80, 81, 249; 137/625.46, 625.18, 625.19, 95

[56] References Cited

U.S. PATENT DOCUMENTS

| | | | |
|---|---|---|---|
| Re. 31,873 | 4/1985 | Howes | 128/674 |
| 1,683,723 | 10/1927 | Myres | 604/32 |
| 2,538,215 | 1/1951 | Stack | 604/32 |
| 2,564,977 | 8/1951 | Hsi Hu | 604/32 |
| 3,297,053 | 1/1967 | McKinney | 137/625.46 |
| 3,316,935 | 5/1967 | Kaiser et al. | 137/595 |
| 3,385,321 | 5/1968 | Ehrens et al. | 137/625.46 |
| 3,595,231 | 7/1971 | Pistor | 128/215 |
| 3,678,959 | 7/1972 | Liposky | 137/625.11 |
| 3,941,126 | 3/1976 | Dietrich et al. | 128/214 R |
| 4,051,867 | 10/1977 | Forberg | 137/595 |
| 4,245,636 | 1/1981 | Sparks et al. | 128/214 R |
| 4,397,335 | 8/1983 | Doblar et al. | 137/625.19 |
| 4,526,343 | 7/1985 | d'Agostino et al. | 251/367 |
| 4,559,036 | 12/1985 | Wunsch | 604/259 |
| 4,568,329 | 2/1986 | Mahurkar | 604/280 |
| 4,581,012 | 4/1986 | Brown et al. | 604/283 |
| 4,602,657 | 7/1986 | Anderson, Jr. et al. | 137/595 |
| 4,604,093 | 8/1986 | Brown et al. | 604/248 |
| 4,624,662 | 11/1986 | Le | 604/249 |
| 4,670,009 | 6/1987 | Bullock | 604/43 |
| 4,674,496 | 6/1987 | Svadjian et al. | 128/207.16 |
| 4,687,475 | 8/1987 | Tai et al. | 604/81 |

*Primary Examiner*—C. Fred Rosenbaum
*Assistant Examiner*—Mark W. Bockelman
*Attorney, Agent, or Firm*—Lynn G. Foster

[57] ABSTRACT

A multi-lumen-catheter flow valve system (10) comprises a catheter (14) having three separated lumens (70, 72, 74), each lumen having a separate outlet opening (122a-c) at a distal end portion of the catheter, and a selective-in/all-out valve apparatus (12). The valve apparatus has red, grey and blue input ports (46, 48, 50) and center, first offset and second offset output ports (64, 66, 68), each of the input ports being selectively coupled to a fluid source (16, 18 or 20) and each of the output ports being coupled to a lumen of the blood vessel catheter. The valve apparatus can be adjusted to selectively transmit fluid(s) entering the three input ports to the three output ports without mixing the fluids and to transmit fluids entering a lesser number of input ports than output ports to the three output ports, also without mixing the fluids.

9 Claims, 3 Drawing Sheets

MULTI-LUMEN-CATHETER FLOW VALVE SYSTEM

BACKGROUND OF THE INVENTION

This invention relates broadly to catheters and more specifically to catheters having a plurality of separated lumens, especially blood vessel catheters.

Quite often, treatment of medical patients requires simultaneous infusion, and/or withdrawal of various fluids from patients' blood streams. Many patients, especially those under intensive care, require simultaneous drug administration, IV feedings, CVP monitoring, and periodic blood sampling. Basically, the rotor 34 is a movable, adjusting device which is used for reducing the number of active input tubes 58, 60, and 62 transmitting fluid in while simultaneously changing connections to the output tubes 76, 78 and 80 so that all of the output tubes continue to transmit fluid out without substantially mixing them. In the past, this has meant that such patients have required insertion of a corresponding number of catheter devices simultaneously coupled to major blood vessels. The implantation of a plurality of catheters involves an undue amount of work for medical personnel and is a source of great discomfort to patients. In addition, the administration of multiple catheters increases the risk of vascular trauma, bleeding, and infection by providing additional passages for infection-causing bacteria.

To overcome these difficulties it has been suggested to employ a single venous catheter device having multiple lumens therein (U.S. Pat. No. Re.31,873 to Howes). Howes points out in this patent that fluids applied through the various lumens of his venous catheter device are often incompatible with one another and for this reason Howe provides that each lumen of his venous catheter has a distal terminus, or outlet opening, spaced along the catheter from the distal termini of the other lumens. Howes points out that such an arrangement allows his plural-lumen venous catheter device to be usable for infusion of more than one fluid simultaneously into a vein of a patient as well as to be used for making withdrawals for CVP measurements. Although the device described in Howes has a number of advantages over separate catheters, it also has some disadvantages. A primary disadvantage of the multiple-lumen venous catheter device described in Howes results from the fact that intravenous treatment of patients varies tremendously over a recovery period. That is, when a patient is first placed under intensive care, he often requires the administration of intravenous fluids and/or medications of various types in each of the catheter's lumens. However, as the patient recovers, some of these fluid transfers can be discontinued while others must be continued. For example, it may become desirable to discontinue one drug infusion while continuing others. When patients are treated with separate catheters, discontinuance of one type of intravenous treatment is not a problem because the catheter used for the discontinued treatment is simply resealed or removed. However, when a multi-lumen venous catheter device, such as is described in U.S. Pat. No. Re 31, 873 to Howes, is used, the lumen for the discontinued fluid transfer cannot be removed because other lumens of the multi-lumen catheter are still being used. When use of one lumen of a multi-lumen catheter is discontinued, blood backs up in the lumen and blood clots are usually deposited therein which ultimately occludes the lumen preventing its further use. Additionally, bacteria gets in these blood clots and causes infection which can then spread throughout the patient's body causing sepsis and death. In order to avoid this, when a multi-lumen catheter is used, with one of the lumens not being used, this not-used lumen must be periodically flushed, with many hospitals dictating that nurses must flush unused lumens during every shift. Further, many hospitals dictate that multi-lumen catheters having unused lumens must be changed more frequently than catheters in which all lumens are used. These procedures are not only very expensive and labor intensive, but also increase risks to patients by additional instrumentation increasing the probability of vascular trauma, bleeding, and infection. Also, in carrying out these procedures, patients are brought under increased discomfort and stress.

Thus, it is an object of this invention to provide a multi-lumen-catheter flow valve system which continuously and automatically flushes every lumen of a multi-lumen catheter, from even a single input lumen, so that the remaining lumens do not have to be specially flushed. This will reduce the incidence of occlusion and infection so that the catheter need not be changed substantially more frequently than are single-lumen blood catheters.

It is also an object of this invention to provide a multi-lumen-catheter flow valve system which is not unduly complicated and which can be relatively inexpensively manufactured.

SUMMARY OF THE INVENTION

According to principles of this invention, a multi-lumen-catheter flow valve system comprises a selective-in/all-out valve apparatus for use with a venous catheter having a plurality of separated lumens. This selective-in/all-out valve can be selectively adjusted to transmit fluids entering any of a plurality of input ports to all output ports without substantially mixing the fluids. In a preferred embodiment, the multi-lumen-catheter flow valve system comprises a triple-lumen catheter and a three input port/three output port selective-in/all-out valve apparatus. The valve apparatus comprises a rotary valve with offset input ports being sequentially disconnected from their respective output ports and a central input port being coupled to the thusly decoupled offset outlet ports while remaining coupled to its central output port.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 4 is a side elevational view of the valve apparatus of FIG. 3;

DESCRIPTION OF PREFERRED EMBODIMENT

A multi-lumen-catheter flow valve system 10 comprises a selective-in/all-out valve apparatus 12, a multi-lumen catheter 14 and various tubes and connectors for interconnecting respective lumens of the multi-lumen catheter 14 with red, grey and blue fluid sources 16, 18 and 20 via the selective-in/all-out valve apparatus 12.

Figure 2:
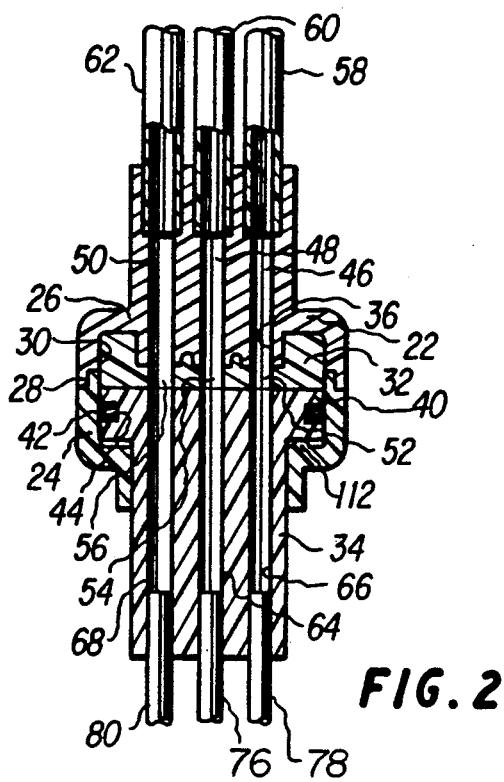
FIG. 2 is a sectional view of a selective-in/all-out valve apparatus of the multi-lumen-catheter flow valve system of FIG. 1.
Figure 3:
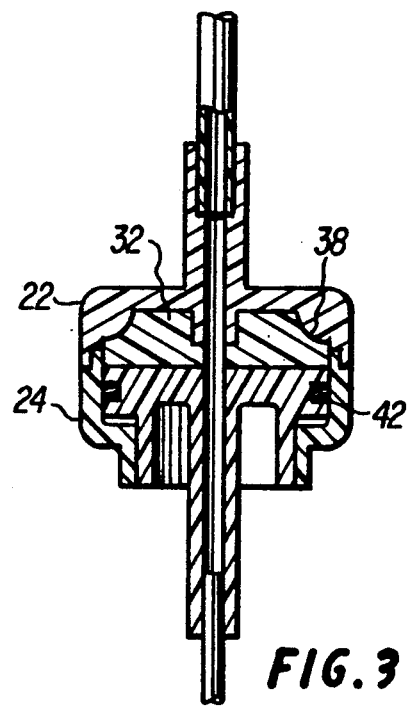
FIG. 3 is a sectional view of the valve apparatus of FIG. 2, but rotated 90° therefrom.
Figure 5:
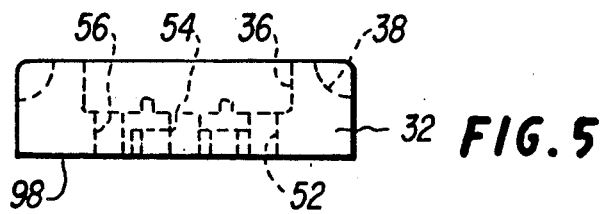
FIG. 5 is a side view of a seal of the valve apparatus of FIGS. 1-4.

The selective-in/all-out valve apparatus 12 comprises a relatively hard resinous plastic housing 22 constructed of a housing bottom 24 which is ultrasonically welded to a housing top 26 at a welding interface line 28. In a preferred embodiment, the housing 22 is constructed of a relatively hard, ABS medical grade, high gloss plastic. As can be seen in FIGS. 2 and 3, the housing 22 defines a circular housing cavity 30 which receives a valve seat or seal 32 and a top portion of a valve rotor 34. The valve seal 32 includes an oblong indentation 36 in its upper surface and notches 38 about its upper periphery for receiving corresponding elements of the housing top 26 to thereby lock the seal in a fixed angular position relative to the housing 22. On the other hand, a flange 40 at the upper end of the rotor 34 has an o-ring 42 in a peripheral o-ring slot 44 for engaging an inner surface of the housing bottom 24 and is free to rotate within the housing cavity 30 while maintaining a seal with the housing 22 via the o-ring 42.

The housing top 26 has a red, a grey, and a blue (all references to passageway colors are denoted as descriptive terms applying to a contiguous nature of fluid flows as opposed to referencing specific colors) passage 46, 48 and 50 therethrough which passages remain aligned with corresponding red, grey and blue passages 52, 54 and 56 of the valve seal 32. In addition, upper ends of the red, grey and blue passages 46, 48 and 50 of the housing top 22 communicate respectively with red, grey and blue fluid sources 16, 18 and 20 via red, grey and blue input tubes 58, 60, and 62.

The rotor 34 has a center passage 64 and first and second offset passages 66 and 68 which are each respectively coupled with a center, a first offset and a second offset lumen 70, 72 and 74 of the multi-lumen catheter 14 via center, first offset, and second offset output tubes 76, 78 and 80, center, first offset and second offset input tubes 82, 84 and 86 of the multi-lumen catheter 14 and their respective adaptor connectors 88 and 90. It should be understood that the terminology "center", "first offset", and "second offset" with regard to the multi-catheter 14 refers to the passages of the rotor 34 to which those elements of the multi-catheter are attached and not to characteristics of the catheter itself.

Figure 6:
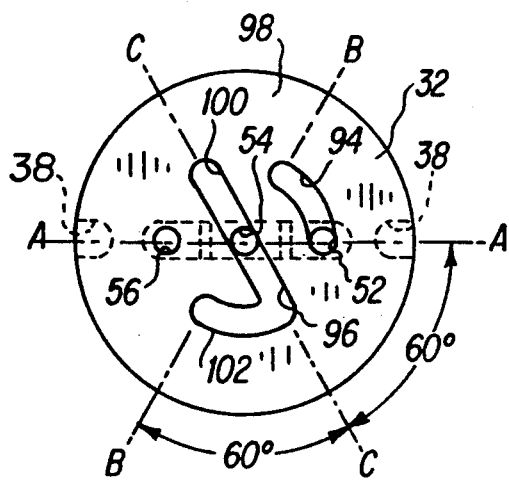
FIG. 6 is a bottom view of the seal of FIG. 5.
Figure 7:
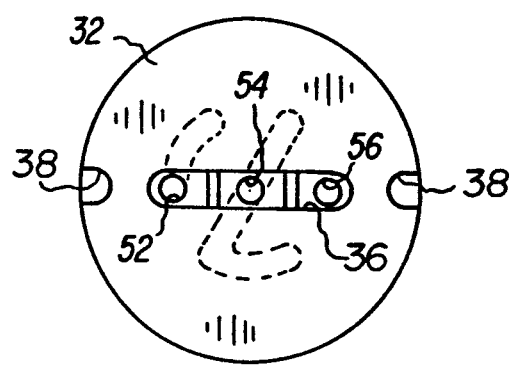
FIG. 7 is a top view of the seal of FIG. 5.
Figure 8:
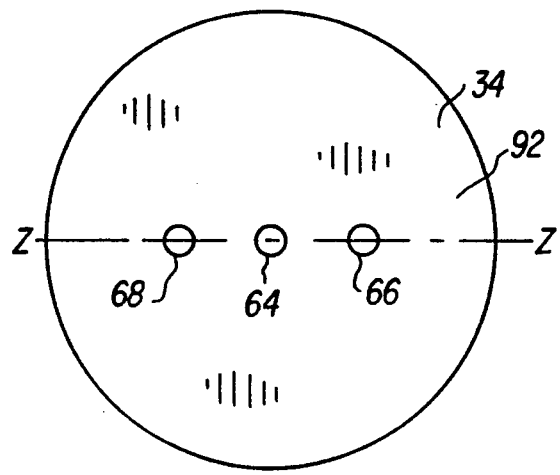
FIG. 8 is a top view of a rotor of the valve apparatus of FIGS. 1-4.
Figure 10:
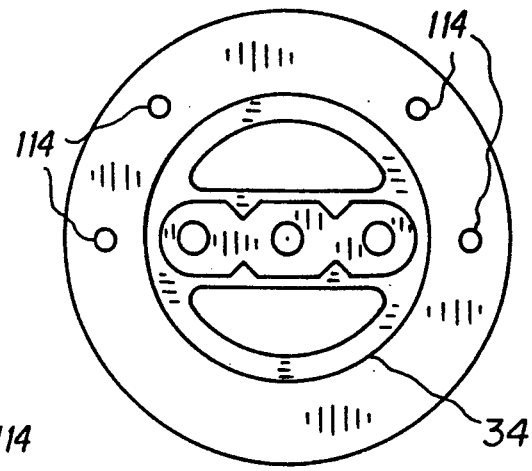
FIG. 10 is a top view of the rotor of FIG. 8.

The rotor 34 and the valve seal 32 are shown in more detail in FIGS. 5-10. In these drawings, it can be seen that the center passage 64, first offset passage 66 and second offset passage 68 of the rotor 34 extend directly through the rotor 34, with bottom ends of these passage being coupled directly to the center, first offset and second offset output tubes 76, 78, and 80 and top ends of these passages exiting the rotor 34 at a relatively smooth top valve face 92 of the rotor 34. On the other hand, the red, grey and blue passages 52, 54, and 56 of the stationary valve seal 32 extend downwardly through the valve seal 32 from the oblong indentation 36. Lower ends of the red and grey passages 52 and 54 respectively communicate with a red groove 94 and a grey groove 96 at a bottom face 98 of the valve seal 32. In this regard, the red and grey grooves 94 and 96 open to the bottom face 98, however, they do not open to the oblong indentation 36 other than at the red and grey passages 52 and 54. In other words, they extend partially through the valve seal 32 toward the oblong indentation 36 but not to the oblong indentation 36. As can be seen in FIG. 6, the red, grey and blue passages 52, 54 and 56 are arranged in a line, with the red groove 94 extending in an arc in a counter clockwise direction from the red passage 52, about the grey passage 54. The grey groove 96 has a straight portion 100 which extends on a 60° angle with the line of the red, grey and blue passages 52, 54 and 56 and an arc portion 102 which extends in a clockwise direction from a lower end of the straight portion away from the red groove 94 about the grey passage 54. The straight portion 100 extends a distance which is at least as great as a distance defined by a line between the red and blue passages 52 and 56. The arc portion 102 extends 60°.

If an angular orientation of the rotor 34 is aligned with an A—A position, as shown in FIG. 2, its center passage 64 and first and second offset passages 66 and 68 respectively align with the grey, red and blue passages 52, 54 and 56 of the seal 32. However, when the rotor 34 is rotated in a left hand direction (or clockwise as viewed in FIG. 8) so that its center and first and second offset passages 64, 66 and 68 align with a position B—B shown in FIG. 6, then the center passage 64 and the second offset passage 68 communicate with the grey groove 96, while the first offset passage 66 continues to communicate with the red passage 52, but now via the red groove 94.

Now assume the rotor is turned 60 more degrees in a left hand direction to the C—C position of FIG. 6 so that the center passage 64 and the first and second offset passages 66 and 68 align with the straight portion 100 of the grey groove 96 and therefore communicate with the grey passage 54 of the seal 32.

Red, grey and blue indicia strips 104, 106 and 108 (FIGS. 4 and 9) which correspond in position to a slot 110 (FIG. 4) in the housing bottom 24 indicate to a user which respective fluids from the red, grey and blue sources 16, 18 and 20 are being transmitted by the selective-in/all-out valve apparatus 12. Additionally, the adaptor connectors 63a, 63b and 63c are colored red, grey and blue respectively to aid users in identifying sources.

Figure 9:
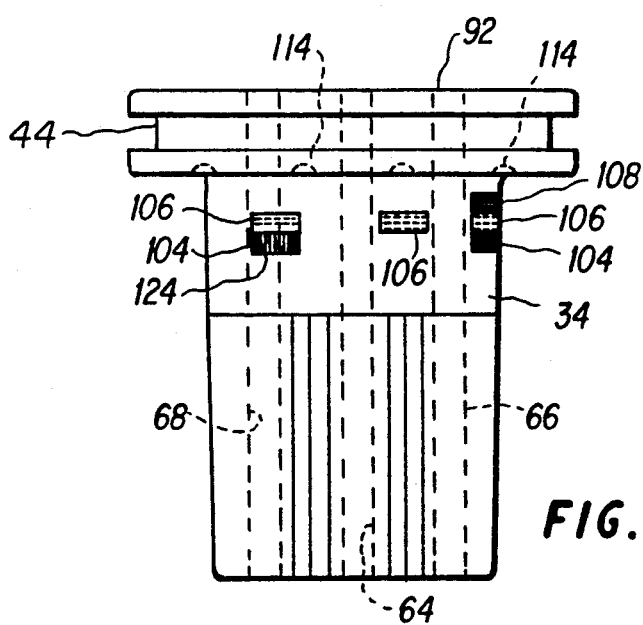
FIG. 9 is a side elevational view of the rotor of FIG. 8.

An embellishment of the selective-in/all-out valve apparatus is in the form of an indicator protrusion 112 (FIG. 2) on an interior surface of the housing bottom 24 which fits into indicator indentations 114 (FIGS. 9 and 10) with which a user can feel when the rotor 34 is in one of the positions A—A, B—B, or C—C. Also in each of these positions, a pattern of indicator strips 104-108 is visible through the slot 110 to inform a user which fluid sources are being transmitted by the selective-in/all-out apparatus 12. Although three representative patterns of indicia strips 104, 106 and 108 are shown in FIG. 9 to represent three different positions of rotation in a right hand direction, in a preferred embodiment, the rotor 34 is actually turned in a left hand direction so that the patterns that are usually seen in the preferred embodiment are on the other side of the rotor and, therefore, cannot be seen in FIG. 9.

It will be understood by those of ordinary skill in the art that various additional "feel" and vision mechanisms could be added to the selective-in/all-out valve apparatus 12, such as stops and the like. Further, it should be understood that in one embodiment the rotor 34 is made to rotate in the left hand direction to achieve various flow-through conditions as was previously described.

Describing now operation of the multi-lumen catheter flow valve system 10, when intensive treatment of a patient 116 is commenced a hollow needle (not shown) is inserted through the patient's skin 118 into a vein 120 of the patient and a distal end of the multi-lumen catheter 14 is inserted thereinto with outlet openings, or termini, 122a, b and c, being substantially linearly spaced from one another along the vein 120. Adaptor connectors 88 of the selective-in/all-out valve apparatus 12 are coupled to the first offset input tube 84, the center input tube 82 and the second offset input tube 86 of the catheter 14 leading to the lumens 70, 72 and 74.

Red, grey and blue fluid sources 16, 18 and 20 are respectively coupled to the adaptor connectors 63a, b and c respectively leading to the red, grey and blue input tubes 58, 60 and 62. It should be understood that the red, grey and blue fluid sources can be medicines, plasmas, and even negative-pressure fluid sources for taking blood. In other words, words such as "source" and "outlet" when used herein can also refer to negative pressure fluids and outlets for negative pressures and should not be limited to mean fluids passing in only one direction therethrough. That is, the red, grey, and blue sources 16, 18 and 20 and the outlet openings 122a, b and c could be used for both disbursing and withdrawing fluids.

In any event, the rotor 34 is initially set in the position shown in FIGS. 2 and 3 in which the red, grey and blue passages 46, 48 and 50 respectively align with the first offset passage 66, the center passage 64, and the second offset passage 68. In this configuration, a blue fluid from the blue fluid source 20 travels through the blue input tube 62, the second offset output tube 80, the second offset input tube 86, the second offset lumen 74, and through the outlet opening 122c into the blood vein 120. Similarly, the grey fluid 18 passes through the grey input tube 60, the center output tube 76, the center input tube 82, the center lumen 70, and through the outlet opening 122b. Also, the red fluid source 16 travels through the red input tube 58, the first offset output tube 78, the first offset input tube 84, the first offset lumen 72, and through the output opening 122a. In this configuration, each of these fluids is maintained separately from the other fluids, all of the lumen of the multi-lumen catheter 14 are substantially continually used, and the fluids are dispensed in the vein 120 separate from one another so that they do not mix thereat.

Now suppose that a doctor directs that the patient no longer be treated with fluid blue. To accomplish this, the rotor 34 is rotated 60 degrees in a left hand direction as viewed in FIG. 9, or in a clockwise direction as viewed in FIG. 8, so that now the second offset passage 68 and the center passage 64 of the rotor 34 both receive fluid from the grey fluid source 18 via the input tube 60. In this regard, as was previously explained, the grey passage 54 of the valve seal 32 now still aligns with the center passage 64 while the blue passage of the valve seal 32 is also connected to the center passage 64 via the arc portion 102 and the straight portion 100 of the grey groove 96. The blue input tube 62 no longer communicates with any of the center, first offset or second offset output tubes 76, 78 or 80, thus, it can be disconnected. The red input tube, however, continues to communicate with the first offset output tube 78, however, via the red groove 94 and the red passage 52, as well as with the first offset lumen 72 and its outlet opening 122a. Fluid from the grey fluid source 18 passes through the center output tube 76 and the second offset output tube 80 into the center lumen 70 and the second offset lumen 74 of the multi-lumen catheter 14. That is, in this configuration as well, all lumen of the multi-lumen catheter 14 continue to be infused although the blue fluid source 20 has been discontinued. In this position of the rotor 34 a pattern of colors 124 (which is actually on the other side of the rotor so that it cannot be seen in FIG. 9), can be seen in the slot 110.

Now assume the doctor prescribes that the patient should no longer be treated with fluid from the red fluid source 16. In this case, a user rotates the rotor 34 either 120 degrees to the right or 60 degrees to the left in which configuration all three of the center passage 64 and first and second offset passages 66 and 68 will align with the straight portion 100 of the grey groove 96 so that fluid from the grey fluid source 18 now feeds through the center output tube 76, the first offset output tube 78 and the second offset output tube 80 into the center lumen 70, the first offset lumen 72 and the second offset lumen 74 respectively. Also in this configuration, all lumen of the multi-lumen catheter 14 are being infused although only one of the fluid sources, that is the grey fluid source 18, is being used. The fluid from the grey fluid source 18 is being proportioned between all lumen of the multi-lumen catheter 14.

In each of the above described orientations of the rotor 34 the indicia strips 104–108 indicate to a user which of the fluid sources is being fed to the lumens of the multi-lumen-catheter 14.

Figure 1:
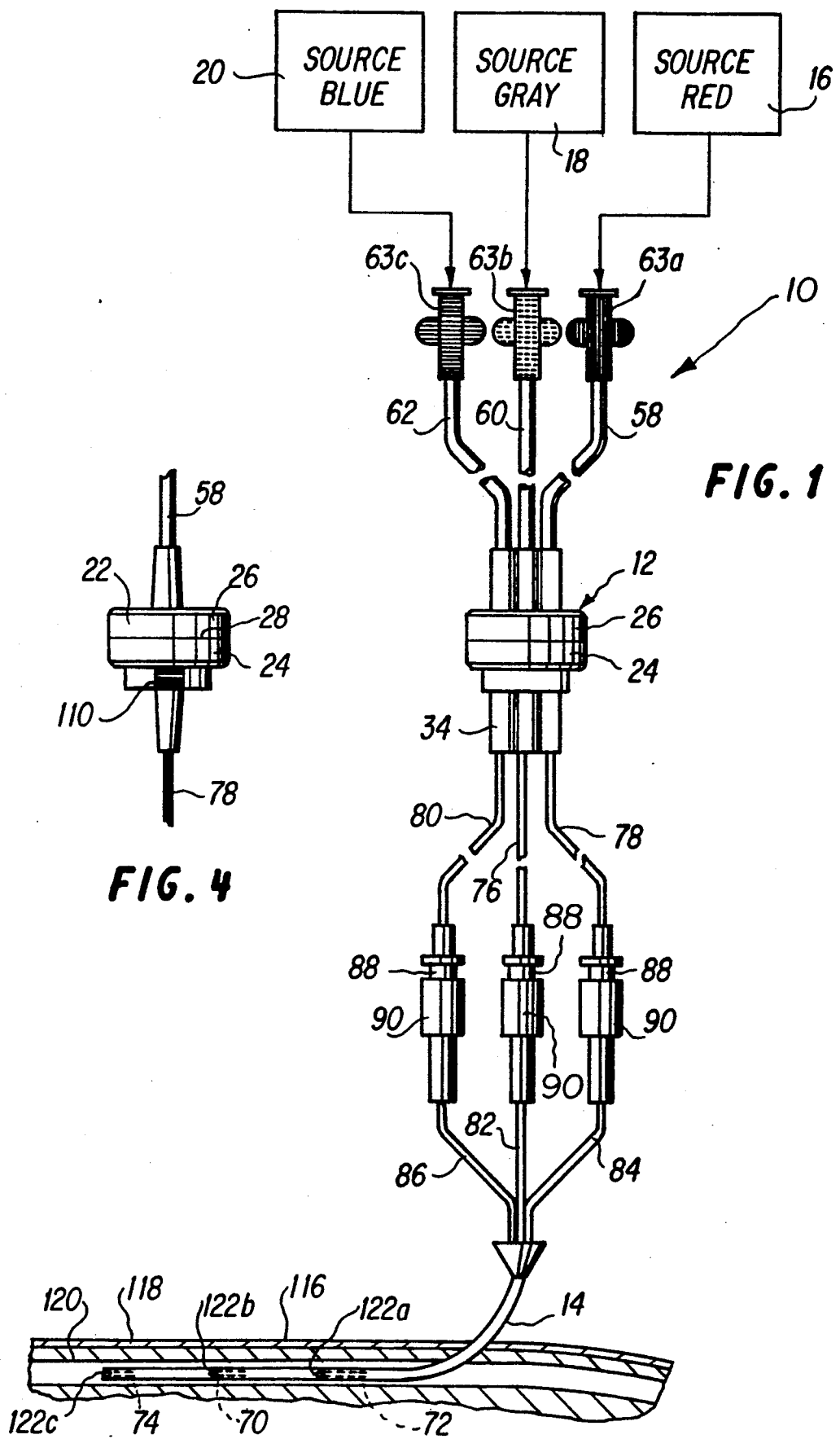
FIG. 1 is a side elevational view, partially in section and partially as a schematic block diagram, of a multi-lumen catheter flow valve system of this invention with a catheter thereof being implanted in a blood vessel.

It can be seen in FIG. 1 that the input tubes 58–62 are larger than the output tubes 76–80 which allows a single input tube to feed multiple output tubes. In this regard, the grey input tube 60 has a cross sectional inside diameter surface area which is approximately the combined sizes of all of the cross-sectional inside diameter surface areas of output tubes 76–80.

It should be appreciated by those of ordinary skill in the art that use of the selective-in/all-out valve apparatus 12 enables medical personnel to discontinue administration of certain fluids without fear of subjecting patients to undue risks from infection or undue stress from frequent changes of, or flushes of, catheters.

By using rotor positions spaced 60° apart a maximum separation between the red, grey and blue passages can be achieved in the selective-in/all-out valve apparatus for a three-lumen catheter.

While the invention has been particularly shown and described with reference to a preferred embodiment, it will be understood by those skilled in the art that various changes in form and detail may be made therein without departing from the spirit and scope of the invention. For example, there are many other types of multi-port valves which could probably be used for this invention. Also, the valve described herein, as well as other valves, could have various stops and indicators thereon to provide feedback to medical personnel as to settings of the valves.

It should be appreciated that when one fluid is no longer administered, this invention automatically flushes a line which had been used to deliver that fluid, thereby reducing infections, labor and stress. This invention accomplishes this without mixing fluids being fed to a patient.

The embodiments of the invention in which an exclusive property or privilege are claimed or defined as follows:

1. A medical multi-lumen-catheter patency maintaining system comprising:
   at least two sources of medical liquid;
   at least two liquid communicating tubes, each liquid communicating tube connected at a proximal end to one of the at least two sources of medical liquid;
   a valve comprising at least two inlet ports, each inlet port being in liquid communication with one of said tubes, said valve further comprising at least two outlet ports;
   a patient insertable catheter comprising at least two lumens and means for connecting a proximal end of the catheter to said outlet ports such that each lumen of said catheter communicates with one outlet port;
   said valve further comprising a single rotary switching element interposed between the inlet ports and the outlet ports for switching pathways of liquid through the valve at at least two switchable positions whereat at a first position each inlet port and therefore each source is only fluidly connected to a different outlet port and therethrough to an individual lumen of said catheter and at a second position one inlet port only is fluidly connected to at least two outlet ports and therethrough to at least two lumens of the catheter thereby providing liquid from one source to at least two lumens of said catheter and liquid from at least one source is supplied to each lumen of the catheter in every switch position.

2. A medical multi-lumen-catheter patency maintaining system according to claim 1 wherein said at least two sources of medical liquid comprise at least three sources of medical liquid, said at least two liquid communicating tubes comprise at least three liquid communicating tubes, said valve comprises at least three inlet ports and at least three outlet ports and said catheter comprises at least three lumens.

3. A medical multi-lumen-catheter patency maintaining system according to claim 2 wherein said interposed element further comprises at least three switchable positions, at least one position connecting liquid from only one source to each lumen of said catheter.

4. A medical multi-lumen-catheter patency maintaining system according to claim 1 wherein said catheter is a venous catheter.

5. A medical multi-lumen-catheter patency maintaining system according to claim 1 wherein the interposed element comprises a main passage connected to only one source through an inlet port for all switch positions.

6. A medical multi-lumen-catheter patency maintaining system according to claim 1 wherein said interposed element comprises a main passage connected to only one source through an inlet port and transversely disposed across an axis of rotation of said rotary switching element for all switch positions.

7. A medical multi-lumen-catheter patency maintaining rotary valve comprising:
   at least two inlet ports one of which is centrally disposed in said valve, each inlet port comprising means for receiving influent liquid from a separate source;
   at least two outlet ports one of which is centrally disposed in said valve along a common axis with the centrally disposed inlet port, at said outlet ports said valve further comprising means for connecting to a multi-lumen-catheter such that each outlet port is in liquid communication with at least one lumen of said catheter;
   rotary means disposed to rotate about said common axis and interposed between the inlet ports and the outlet ports for switching liquid at at least two switchable positions where at a first position each inlet port and therefore influent liquid from each separate source is only connected in liquid communication to a predetermined separate outlet port and at a second position the centrally disposed inlet port is connected in liquid communication to at least two outlet ports without liquid communication with any other inlet port, said rotary means further comprising means for maintaining each inlet port selectively connected in liquid communication to said predetermined outlet port if said outlet port is not otherwise connected to the centrally disposed inlet port.

8. A medical rotary valve according to claim 7 wherein said at least two inlet ports comprise at least three inlet ports and at least two outlet ports comprise at least three outlet ports.

9. A medical rotary valve according to claim 7 wherein said interposed rotary switching means further comprise at least three switchable positions, at least one position for liquid communication from said centrally disposed inlet port to each outlet port.

* * * * *